United States Patent [19]

Hucul et al.

[11] Patent Number: 4,762,858

[45] Date of Patent: Aug. 9, 1988

[54] SYNGAS CONVERSION TO OXYGENATES BY REDUCED YTTRIUM/LANTHANIDE/ACTINIDE-MODIFIED CATALYST

[75] Inventors: Dennis A. Hucul; Rex R. Stevens, both of Midland, Mich.

[73] Assignee: The Dow Chemical Company, Midland, Mich.

[21] Appl. No.: 925,456

[22] Filed: Oct. 31, 1986

Related U.S. Application Data

[63] Continuation of Ser. No. 776,307, Sep. 16, 1985, abandoned.

[51] Int. Cl.$^4$ .............................................. C07C 27/06
[52] U.S. Cl. .................................. 518/714; 518/728; 302/302
[58] Field of Search ................................ 518/714, 728

[56] References Cited

U.S. PATENT DOCUMENTS

| | | |
|---|---|---|
| 1,201,850 | 10/1916 | Mittasch et al. |
| 1,558,559 | 10/1925 | Mittasch et al. |
| 1,569,775 | 1/1926 | Mittasch et al. |
| 1,859,244 | 5/1932 | Patart . |
| 2,490,488 | 12/1949 | Stewart . |
| 2,534,018 | 12/1950 | Gresham . |
| 2,535,060 | 12/1950 | Gresham . |
| 2,539,414 | 1/1951 | Frankenburg . |
| 2,787,628 | 4/1957 | Himmler et al. |
| 2,821,537 | 1/1958 | Rottig . |
| 3,673,114 | 6/1972 | Allum et al. |
| 3,842,113 | 10/1974 | Ichikawa et al. |
| 3,842,121 | 10/1974 | Ichikawa et al. |
| 3,850,840 | 11/1974 | Aldridge et al. |
| 3,928,000 | 12/1975 | Child et al. |
| 4,096,164 | 6/1978 | Ellgen et al. |
| 4,122,110 | 10/1978 | Sugier et al. |
| 4,151,190 | 4/1979 | Murchison et al. |
| 4,151,191 | 4/1979 | Happel et al. |
| 4,162,262 | 7/1979 | Ellgen et al. |
| 4,168,276 | 4/1979 | Finch . |
| 4,175,928 | 11/1979 | Britton et al. |
| 4,177,202 | 12/1979 | Chang et al. |
| 4,199,522 | 4/1980 | Murchison et al. |
| 4,210,597 | 7/1980 | Huang . |
| 4,219,445 | 8/1980 | Finch . |
| 4,243,553 | 3/1981 | Naumann et al. |
| 4,243,554 | 3/1981 | Naumann et al. |
| 4,260,553 | 4/1981 | Happel et al. |
| 4,261,864 | 2/1981 | Hargis . |
| 4,298,354 | 11/1981 | Hardman et al. |
| 4,348,486 | 9/1982 | Calvin et al. |
| 4,362,821 | 12/1982 | Lin . |
| 4,380,589 | 4/1983 | Murchison et al. |
| 4,440,668 | 4/1984 | Chang et al. |
| 4,451,579 | 5/1984 | Lemanski et al. |
| 4,459,369 | 7/1984 | Passariello . |
| 4,478,954 | 10/1984 | Connolly et al. |
| 4,511,674 | 4/1985 | Pederson et al. |
| 4,513,096 | 4/1985 | Connolly et al. |
| 4,513,100 | 4/1985 | Fattore et al. |
| 4,544,673 | 10/1985 | Lemanski et al. |
| 4,562,174 | 1/1985 | Stiles . |

FOREIGN PATENT DOCUMENTS

| | | |
|---|---|---|
| 251483 | 7/1925 | Canada . |
| 1139789 | 1/1983 | Canada . |
| 5492 | 11/1979 | European Pat. Off. . |
| 0030110 | 6/1981 | European Pat. Off. . |
| 0119609 | 4/1984 | European Pat. Off. . |
| 0149255 | 7/1985 | European Pat. Off. . |
| 0149256 | 7/1985 | European Pat. Off. . |
| 2533554 | 3/1984 | France . |
| 59-170023 | 4/1984 | Japan . |
| 238319 | 8/1925 | United Kingdom . |
| 254760 | 7/1926 | United Kingdom . |
| 275345 | 8/1927 | United Kingdom . |
| 293056 | 6/1928 | United Kingdom . |
| 317804 | 10/1930 | United Kingdom . |
| 313093 | 12/1930 | United Kingdom . |
| 1501892 | 2/1978 | United Kingdom . |
| 2065491 | 7/1981 | United Kingdom . |
| 2076015 | 11/1981 | United Kingdom . |
| 2076423 | 12/1981 | United Kingdom . |

OTHER PUBLICATIONS

Catalytica Associates, Inc., "A Critical Analysis of Recent Advances in CO–H$_2$ Catalysis", Multiclient Study No. 1124 (Jun. 1980).
Diffenbach et al., "Synthesis Gas Conversion to Liquid Fuels Using Promoted Fused Iron Catalysts", DOE/-PETC/TR-81/3 (Sep. 1981).
Greene C.E.P., 46–51 (Aug. 1982).
Kummer et al., vol. 73, pp. 564–569 (Feb. 1951).
Kummer et al., vol. 75, pp. 5177–73 (Nov. 5, 1953).
Mills et al., "Catalytic Methanation", *Catalysis Rev.*, 8(2), 159–210 (1973).
Morgan et al., *J. Soc. Chem. Ind.*, 51 1T–7T (1932).
Sheldon, "Chemicals from Synthesis Gas", Reidel, Boston, 185–196 (1983).
Tatsumi et al., *Chem. Letts., Chem. Soc. Japan*, (5) 685–688 (1984).
Shultz et al., "Noble Metals, Molybdenum and Tungsten in Hydrocarbon Synthesis", Bureau of Mines Report of Investigations 6974.
Anderson et al., Industrial and Engineering Chemistry, vol. 44, No. 10, pp. 2418–2424, and pp. 391–401, (vol. 44, No. 2).
Engineering & Process Development, "Fischer–Tropsch Synthesis", Anderson et al., pp. 391–401.

*Primary Examiner*—Howard T. Mars
*Attorney, Agent, or Firm*—Charles J. Enright

[57] ABSTRACT

A process for the conversion of a mixture of synthesis gas into preponderantly $C_{1-10}$ oxygenated hydrocarbons and especially $C_{1-5}$ mixed alcohols using a reduced catalyst of the necessary components of (1) niobium, tantalum, molybdenum, tungsten, technetium and/or rhenium; and
(2) yttrium, a lanthanide and/or actinide series metal;

and the optional components of
(3) a promoter; and/or
(4) a support.

High synthesis gas conversions are possible in large part due to the high catalytic activity of the reduced catalyst. The reduced catalyst composition itself with yttrium as cocatalyst metal or promoted with special levels of a Fisher-Tropsch promoter.

7 Claims, No Drawings

SYNGAS CONVERSION TO OXYGENATES BY REDUCED YTTRIUM/LANTHANIDE/ACTINIDE-MODIFIED CATALYST

CROSS REFERENCE TO RELATED APPLICATION

This is a continuation in part of application Ser. No. 776,307 filed Sept. 16, 1985, now abandoned.

FIELD OF THE INVENTION

This invention relates to a process for production of $C_{1-10}$ oxygenated hydrocarbons from synthesis gas. The invention also relates to a catalyst.

BACKGROUND OF THE INVENTION

Many examples of compositions useful as catalysts involved in oxygenated hydrocarbon manufacture and processing are known. Some catalysts are especially useful in production of $C_{1-10}$ oxygenated hydrocarbons from synthesis gas (i.e., syngas), which comprises a gaseous mixture of carbon monoxide and hydrogen. Some are most especially useful in processes for production of $C_{1-5}$ oxygenated mixed alcohols. Much of the art relating to these processes is concerned with the production of catalysts which enhance productivity when used therein. Especially in processes which convert synthesis gas into $C_{1-10}$ oxygenates and most especially in mixed alcohols processes, enhancement of productivity generally relates to improving conversion, the amount of carbon monoxide converted into product, or improving selectivity, the amount of carbon monoxide converted to a given desired product divided by the amount of total carbon converted excluding carbon dioxide by-product. Such a composition which enhances productivity, especially in converting synthesis gas into oxygenated hydrocarbons and in a mixed alcohols process in particular, has a greater catalytic activity in the process in which it is used. The elements and method used to produce such compositions can affect its utility and activity.

For example, Stewart, U.S. Pat. No. 2,490,488 (1949) (incorporated herein by reference), discloses a catalyst made from molybdenum disulfide promoted with an alkali or alkaline earth metal compound, but not alumina or thoria, useful in a Fischer-Tropsch process and discloses that when the catalyst is not so promoted it is useful in a methanation process. The example shows a 30 percent selectivity to $C_{3+}$ (i.e., of three carbon atoms and higher) hydrocarbons and oxygenates. Of this 30 percent, at most 14 percent boils near or above 65° C., the boiling point of methanol. Thus, alcohol selectivity is at a maximum of 13.2 percent.

Kinkade (Union Carbide), European Patent Application No. 84116467.6 (published July 24, 1985, Publ. No. 149,255) (incorporated herein by reference), discloses that $C_{1-5}$ n-alcohols are substantially produced with a catalyst consisting essentially of molybdenum sulfide and an alkali metal compound. The gas hourly space velocity (i.e., GHSV) must be about 3000 hour$^{-1}$ or above. Variations in the GHSV, temperature, pressure and alkali metal compound are disclosed to affect the alcohols' selectivity.

Pedersen et al., British Patent Publication No. 2,065,291 (incorporated herein by reference), disclose a process for making $C_2$ hydrocarbons from syngas using a catalyst comprising a group VB or VIB metal in combination with an iron group metal, as free metals, oxides or sulfides on a porous oxidic support. The authors note that the presence of hydrogen sulfide alters the activity and selectivity of their process.

Happel et al., U.S. Pat. No. 4,151,191 (1979) and U.S. Pat. No. 4,260,553 (1981) (both incorporated herein by reference), disclose methanation processes with certain unreduced, unpromoted molybdenum and lanthanide- or actinide-containing catalysts.

Hargis, U.S. Pat. No. 4,261,864 (1981) (incorporated herein by reference), teaches a process for making α-olefins from syngas over an iron tungstate/alkali metal hydroxide catalyst.

Chang et al., U.S. Pat. No. 4,177,202 (1979) (incorporated herein by reference), teach a process for making methane- or ethane-rich hydrocarbons from syngas over a molybdenum catalyst, optionally promoted with cobalt or vanadium. Selectivity to ethane is enhanced by the presence of hydrogen sulfide in the syngas feed.

Murchison et al., U.S. Pat. No. 4,151,190 (1979); U.S. Pat. No. 4,199,522 (1980); and U.S. Pat. No. 4,380,589 (1983) (all incorporated herein by reference), disclose Fischer-Tropsch processes for the production of $C_{2-4}$ hydrocarbons and $C_{2-4}$ olefinic hydrocarbons with certain Fischer-Tropsch catalysts which contain Mo, W and or Re and an alkali, alkaline earth and/or thorium promoter. Commercially significant quantities of oxygenates such as alcohols from these catalyzed processes are not taught Hydrogen sulfide is taught to affect the catalyst activity.

Anderson et al., *Industrial and Engineering Chemistry*, Vol. 44, No. 10, pp. 2418–2424 (incorporated herein by reference), disclose a number of catalysts containing zinc, copper, chromium, manganese, thorium, iron, occasionally promoted with alkali or other materials for making various alcohols. The authors state that ethyl alcohol is a major constituent, the yield of methanol is usually very small and a tentative summary of factors favoring the production of alcohols is high pressure, low temperature, high space velocity, high recycle ratio and carbon monoxide-rich synthesis gas.

Naumann et al., U.S. Pat. No. 4,243,553 (1981) and U.S. Pat. No. 4,243,554 (1981) (both incorporated herein by reference), teach certain thermally decomposed hydrocarbylammonium thiomolybdate and oxythiomolybdate catalysts. The catalyst is especially useful for the water gas shift and methanation reactions.

Quarderer et al. (Dow Chemical), European patent application No. 84102932 5 (published Sept. 26, 1984, Publ. No. 119,609) (incorporated herein by reference), discloses that alcohols which boil in the range of motor gasoline are made at good selectivities from syngas with an optionally supported Mo/W/Re and alkali/alkaline earth element catalyst. In certain preferred embodiments, it is disclosed that Mo/W/Re sulfides and carbon supports, when the catalyst is supported, are each favored, and it is preferred to exclude lanthanide and actinide series metal components.

To make a commercially significant $C_{1-10}$ oxygenated hydrocarbon or alcohols process, one must use a catalyst and conditions which are highly efficient To be efficient, the catalyst must yield a high weight ratio of product per unit weight of catalyst in a given period of time. The catalyst must be stable and active for long periods of time between regenerations. This may be particularly difficult to accomplish, especially for alcohols, when the $H_2/CO$ ratio of the feed gas is low, such as less than 2 to 1. Ideally the catalyst will be sulfur tolerant and will have a high selectivity to a commercial product to avoid purification, removal of by-products or separation into two or more product streams.

When the mixed alcohols product is to be used as a fuel replacement or a fuel additive, it may be desirable that the ratio of $C_1$ to $C_{2+}$ alcohols be no greater than a certain amount. Excessive methanol is generally considered an unattractive additive to gasolines. Methanol may decrease drivability and may increase corrosion in the fuel system and may cause phase separation when used in excessive quantities. These problems may be alleviated by blending methanol with higher alcohols.

Accordingly, one may wish to synthesize mixed alcohols with no more than a certain amount of methanol in the blend. Or in a similar fashion, one may wish to minimize the ratio of $C_1$ to $C_{2+}$ alcohols in mixed alcohols so that methanol may be purchased and blended into the mixed alcohols to give the maximum acceptable $C_1$ to $C_{2+}$ alcohols ratio.

A problem in the art is enhancing the efficiency of the overall processes. This includes increasing conversion and selectivity to desired oxygenated hydrocarbon products. And so, improvements in production of $C_{1-10}$ oxygenated hydrocarbons are always needed and welcome. They are especially needed and welcome when they are the result of a composition with enhanced and improved catalytic activity and selectivity being used therein.

SUMMARY OF THE INVENTION

The invention is a process for producing preponderantly products of $C_{1-10}$ oxygenated hydrocarbons comprising contacting a mixture of synthesis gas in the presence of a catalytic amount of a reduced catalyst composition which comprises necessary components of:

(a) a catalyst metal of Nb, Ta, Mo, W, Tc, Re or combination thereof, in free or combined form; and
(b) a cocatalyst metal of yttrium, a lanthanide or actinide series metal, or combination thereof, in free or combined form, under conditions such that said products are produced.

Another aspect of the invention is the reduced catalyst composition with the cocatalyst metal yttrium or the reduced catalyst composition promoted with a Fischer-Tropsch promoter at a level of about 0.5 percent by weight or above.

The invention has utility as a process which produces well-known products useful as combustibles, solvents and/or polymer intermediates. For example, ethanol may be used as an additive to gasoline or solvent.

The process of the invention is extremely efficient in conversion of synthesis gas and flexible in selectivity to certain products. Surprisingly, the process demonstrates high conversion and flexible selectivity because of the activity of catalyst composition of the invention used therein. The flexible selectivity of the catalyst composition is attributed to its preferable sensitivity to differences in the amount of an optional promoter present. The catalyst composition shows high activity, and the process shows the high conversion in large part due to the reduction of the catalyst composition. The process may surprisingly result in increased selectivity to $C_{1-10}$ mixed alcohols, and it may be used to prepare $C_{2+}$ alcohols in high selectivity.

DETAILED DESCRIPTION OF THE INVENTION

The catalyst metals of the invention are selected from Nb, Ta, Mo, W, Tc and Re. The catalyst metal may be present in free or combined form.

In free or combined form herein means the metal component of interest may be present as a metal, alloy, compound, adduct or combination thereof. Representative compounds include hydroxides, oxides, sulfides, sulfates, halides, carbides, cyanides, nitrides, nitrates, phosphates, borides, silicides, silicates, oxyhalides, carboxylates such as acetates and acetylacetates, oxalates, carbonates, carbonyls, hydrides, metal-bridged and cluster compounds, compounds where the metal is part of an anionic or cationic species, and the like. Adducts are chemical addition products. Most commonly molecules of polar or electron-donating solvent, former solvent or ligands such as ammonia, aliphatic or aromatic amines, imines, amino alcohols, carboxylic acids, amino acids, di- and trialkyl- and triarylphosphines, -arsines and stibines and their oxides, thiols, amino thiols and the like as is known in the art may add to the catalyst metals as otherwise herein described, with or without displacement.

The free metal and metal oxides, sulfides and carbides are preferred forms of the catalyst-metal in the finished composition with the free metal and metal oxides more preferred. The free metal is most preferred as generally present, especially after reduction, most especially with flowing hydrogen. A preferred group is Nb and Ta. Another preferred group is Mo, W, Tc and Re. Molybdenum is the most preferred catalyst metal.

The catalyst metal is present in an amount such that the composition is useful as a catalyst as herein described. The catalyst metal is preferably generally present at lower limits of about 1 percent, more preferably of about 10 percent, most preferably of about 20 percent and especially of about 30 percent. Equivalent preferable upper limits are of about 99 percent, more preferably of about 90 percent, most preferably of about 80 percent and especially of about 75 percent.

The percentages of each composition component described herein are weight percent on a free metal basis in the finished catalyst unless otherwise specified. However, the components may not necessarily be and often are not present as the free metal. For any supports the reported percentage is a weight percent calculated by taking the ratio of the mass of the dry support in the general form present before contact with the catalyst metal, cocatalyst metal and promoter, in the numerator, and the mass of all composition components in the denominator, and reporting on a percent basis.

The cocatalyst metals of the invention are selected from yttrium and the lanthanide and actinide series metals and may be present in free or combined form. The lanthanide series metals herein are La, Ce, Pr, Nd, Pm, Sm, Eu, Gd, Tb, Dy, Ho, Er, Tm, Yb and Lu. The actinide series metals herein are Ac, Th, Pa, U, Np, Pu, Am, Cm, Bk, Cf, Es, Fm, Md, No and Lr. Preferred cocatalyst metals are the lanthanides and Th. Th is most preferred.

The cocatalyst metal herein is present in an amount such that the composition is useful as a catalyst as herein described. The cocatalyst metal is preferably generally present at lower limits of about 1 percent, more preferably of about 10 percent, most preferably of about 20 percent and especially of about 30 percent. Equivalent preferable upper limits are of about 99 percent, more preferably of about 90 percent, most preferably of about 80 percent and especially of about 70 percent.

Preferred molar ratios of catalyst:cocatalyst metals are at a lower level of 4:1, more preferably 2:1. Equivalent preferable upper levels of the molar ratios are 1:4, more preferably 1:2.

Optional components of the reduced catalyst composition include a promoter and a support.

The optional promoters of the invention include Fischer-Tropsch promoters. Fischer-Tropsch promoters enhance selectivity to $C_{2+}$ products, especially alcohols, characteristically increasing the basicity of the catalyst. During product-forming contact with the synthesis gas, preferred Fischer-Tropsch promoters resist volatilization from the catalyst.

Exemplary Fischer-Tropsch promoters are alkali and alkaline earth metals which may be present in free or combined form. The alkali metals herein include Li, Na, K, Rb and Cs. The alkaline earth metals herein include Be, Mg, Ca, Sr and Ba. The alkali metals are preferred members of this exemplary group, with cesium and potassium more preferred. Potassium is most preferred.

The promoter herein is present in an amount that promotes the catalytic properties of the composition as herein described. The alkali and alkaline earth promoter is preferably generally present at lower limits of about 0.01 percent, more preferably of about 0.1 percent and most preferably of about 0.5 percent. Equivalent preferred upper limits are of about 20 percent, more preferably of about 2 percent.

Usually, as the percent of promoter incrementally increases, the selectivity shifts toward production of more of the $C_{2+}$ products in a process converting synthesis gas. Concurrently, however, overall activity usually declines and water production typically rises.

The promoter is preferably added by the incipient wetness technique or by coprecipitation with the preparative compounds of the catalyst and cocatalyst metals. Incipient wetness is most preferred. Most preferably, the promoter is added by a wet technique such as incipient wetness after the initially made catalyst composition has been dried. It is especially preferred that after such incorporation of the promoter by a wet technique, the composition be treated with a flowing atmosphere especially such as herein described. It is contemplated that the form of the composition containing the added promoter or the form of the promoter may change after such treatment, possibly resulting in further chemical interaction among promoter, catalyst metal, cocatalyst metal and support, if a support is present.

Certain promoters may be added in the form of a support. For example, carbon supports made from coconut shells may contain small amounts of alkali metal.

An additional support is an optional component of the catalyst composition. By additional supports, it is meant that the support at hand is not composed of lanthanide or actinide series components. Examples of additional supports include alumina, carbon, chromia, magnesia, silica, titania and zinc oxide. Combinations of supports may be useful, for example, in cases such as where particular product distributions are desired or where a support which does not have superior crushing resistance in a reactor is mixed with a support that does.

The additional support when present is present in an amount that allows the catalytic activity of the invention. The additional support when present may be present in amounts above about 2 percent, even above about 20 percent. When an additional support is present, a preferred upper limit of the additional support is about 90 percent, more preferably about 60 percent.

Most preferably, the reduced catalyst composition does not contain an additional support in an amount above about 2 percent. This preference is herein termed an additionally unsupported reduced catalyst composition. It is especially preferred that the additionally unsupported condition results from not adding any additional support.

If an additional support is present, the other components are combined with it by methods known in the art. A preferred method is the incipient wetness technique. Evaporation under reduced pressure may be advantageous.

The catalyst composition can be initially made by a variety of techniques that result in intimate contact of the compounds. Examples include: vapor deposition; intimate physical mixing such as dry grinding, powderizing and/or pressing; trituration; paste extrusion mixing; impregnation onto additional supports from an aqueous and/or nonaqueous solvent or carrier as by a slurry; impregnation of one or more components onto another without an additional support such as catalyst metal deposition onto a cocatalyst metal oxide (e.g., aqueous $MoO_3$ onto thoria); coprecipitation; and the like.

One preferred method is to simply mix (with or without solvent or carrier) a preparative compound of the catalyst metal (e.g., $MoO_3$, $(NH_4)_6Mo_7O_{24}$) with a preparative compound of the cocatalyst metal (e.g., La($NO_3)_3$, $ThO_2$) and then heat the mixture (e.g., in air from about 500° C. to about 1500° C.), optionally followed by wet impregnation with promoter. A second preferred method is to precipitate the preparative compounds of the catalyst and cocatalyst metals from solution such as by the addition of La($NO_3)_3$ to a solution containing the $MoO_4^{-2}$ ion which can be made by the addition of ammonium hydroxide to an aqueous solution of $MoO_3$. Addition of the promoters then may follow.

A preparative compound of the catalyst metal or of the cocatalyst metal is a catalyst or cocatalyst metal of the invention in free or combined form which is used in the preparation of the reduced catalyst composition. Preferred preparative compounds of the catalyst metal and cocatalyst metal include oxygen- and nitrogen-containing ionic compounds.

Preferred ranges of temperature under which the catalyst composition is initially made are from about minus 120° C. to about plus 100° C., more preferably from about 0° C. to about 40° C., and most preferably about ambient temperature.

Preferred ranges of pressure during the preparation of the catalyst composition are from $1 \times 10^{-10}$ atmospheres to about 1,000 atmospheres, more preferably from about $1 \times 10^{-7}$ atmospheres to about 10 atmospheres and most preferably about ambient pressure.

To make the initially made catalyst composition into the reduced catalyst composition, it must be reduced, preferably by hydrogen treatment at high temperatures. More preferably, such hydrogen treatment has a lower temperature limit of about 400° C., more preferably about 500° C. Equivalent upper preferable limits are of about 1200° C., more preferably about 700° C.

Other known methods of reduction may be employed. Examples may include contact of the initially made catalyst composition with other reducing atmospheres such as deuterium, carbon monoxide, methane, inert gases containing such reducing gases or others, and the like; liquid phase reducing agents such as hydrazine and hydroxylamine; many metal hydrides; dispersions of free alkali and alkaline earth metals; reducing agents as commonly formed in solutions, such as in water, of a greater reduction potential in the electromotive series than the initially made catalyst composition; and the like.

The reduced catalyst may be regenerated by reductive treatment (e.g., hydrogen) after it has been used for an extended period. Such regeneration, especially with hydrogen, often increases activity.

Additionally, the composition may be treated with flowing air, hydrogen sulfide, nitrogen, oxygen or other atmosphere at ambient or preferably elevated temperatures. Preferably, such additional treatment is done before the reduction. It is more preferred such atmospheric treatment be done at temperatures from about 100° C. to about 800° C.

In the case of potentially combustible supports, suoh as carbon, it is preferred that any such atmospheric treatment be initially done at a temperature range of from about 100° C. to about 130° C., increasing the temperature periodically to about from 170° C. to 190° C. For example, about an hour at from about 110° C. to about 130° C. followed by several hours at from about 170° C. to about 190° C. may be employed. Hydrogen atmosphere treatment as above may then follow.

When reduced, as is known in the art, preferably with hydrogen under reductive conditions such as illustrated in the examples, the composition preferably shows high activity when used in a catalyst in a process for producing preponderantly $C_{1-10}$ (i.e., from carbon number one to carbon number ten, inclusive) oxygenated hydrocarbons, more preferably preponderantly $C_{1-5}$ alcohols; from synthesis gas under reactive conditions. Similarly, the reduced composition additionally promoted with an effective amount of a Fischer-Tropsch promoter, notably potassium, preferably shows high activity when used as a catalyst in the FischerTropsch process, especially for producing preponderantly $C_{2-5}$ alcohols.

Reactive conditions are those known in the art or herein described, such as generally illustrated in the examples, more especially wherein the synthesis gas consists of about 95 mole percent elemental hydrogen and carbon monoxide gases at an $H_2/CO$ molar ratio of about 0.7 and about 5 mole percent dry elemental nitrogen, GHSV corrected to standard temperature and pressure (i.e., STP) of about 500 hour$^{-1}$ temperature of about 300° C. and pressure of about 1000 psig, with no recycle.

An effective amount of a Fischer-Tropsch promoter is that amount required to be added to obtain the desired activity and selectivity. Preferably, it is an amount of about 1.5 percent of the mass of the catalyst and cocatalyst metal after addition of any amount required to neutralize an acidic additional support or about 1.5 percent of the mass of the catalyst metal if the additional support is considered neutral or alkaline.

This surprising activity is preferably about $5 \times 10^7$ units or above, more preferably about $8 \times 10^7$ units or above and most preferably about $1 \times 10^8$ units or above wherein activity as defined herein is as generally defined by Anderson et al., *Ind. Eng. Chem.*, 44(2), 391–401 (1952) (which pages are herein incorporated by reference). In particular, $$\text{Activity} = -GHSV \frac{\ln(1-C)}{P} e^{E/RT}$$

wherein
GHSV is the gas hourly space velocity in units of hour$^{-1}$ as if at STP;
ln(1-C) is the natural logarithm of the quantity (1-C);
C is the fraction of synthesis gas converted into products excluding carbon dioxide;
e is the real number of which the natural logarithm is one;
E is the activation energy (e.g., 22,000 cal/mole for the process of converting the synthesis gas into $C_{1-5}$ alcohols);
R is the gas constant (i.e., e.g., 1.987 cal/mole ° K.);
T is the temperature in degrees Kelvin (i.e., ° K.); and
P is the pressure of the feed synthesis gas in units of atmospheres.

A generally more basic composition favors the production of $C_{2-5}$ alcohols from synthesis gas, but the catalyst activity may decline. The additionally unsupported reduced catalyst composition favors production of $C_{1-10}$ aliphatic oxygenated products, especially $C_{1-5}$ mixed alcohols.

When the reduced catalyst composition is used in syngas conversions, the conversion of carbon monoxide can be unusually high. Notably, such conversion can be about 50 percent or above, more notably about 65 percent or above and most notably about 80 percent or above.

However, conversions are best kept at lower levels in order to enhance production of the oxygenates, especially the $C_{1-5}$ alcohols. Preferably, conversion is adjusted to a lower level of about 10 percent and upwards to an upper level of about 30 percent. More preferably the conversion is from about 15 to about 25 percent. The conversion may be adjusted by adjusting conditions including recycle ratios and space velocity.

Oxygenated hydrocarbons herein are aliphatic or aromatic compounds, otherwise hydrocarbons which contain at least one oxygen bound to carbon therein and include alcohols, ethers, carboxylic acids, esters, ketones, aldehydes, peroxides and cyclic versions thereof. Aliphatic oxygenates are preferred.

Alcohols herein are aliphatic or aromatic compounds, otherwise hydrocarbons which contain at least one hydroxy functionality bound to any carbon therein and generally does not include compounds present as esters or aldehydes. For example, the methanol portion of methyl acetate is not counted as methanol. Thus, phenols are herein alcohols. Aliphatic alcohols are preferred. The mixed alcohol fraction usually formed in the mixed alcohols synthesis may contain methanol, ethanol 1-propanol, 2-propanol, 1-butanol, 2-butanol, 2-methyl-1-propanol, 2-methyl-2-propanol, other $C_{2-4}$ alcohols and $C_{5-10}$ alcohols.

Preferably the selectivity to $C_{2-5}$ alcohols is high while the selectivity to methanol is low. The preferred product mixture, especially as formed under preferred conditions, contains only small portions of other oxygenated compounds besides alcohols. These other compounds may not be deleterious to using the product, as is, in motor fuels.

As used herein, the word "preponderantly" means having greater percent $CO_2$-free carbon selectivity in the described product sample than the percent $CO_2$-free carbon selectivity in any single pure compound by-product of the process other than a compound of the described product sample itself. For example, if the described product sample is $C_{2-5}$ alcohols and they are produced at an agglomerated 40 percent $CO_2$-free carbon selectivity, and the other by-products are methane at 39, methanol at 11 and other hydrocarbons and oxygenated hydrocarbons at an agglomerated 10 percent $CO_2$-free carbon selectivity, the $C_{2-5}$ alcohols would be preponderantly produced. Percent $CO_2$-free carbon selectivity refers to the percent of carbon in a specified product sample with respect to the total carbon converted from carbon monoxide into products other than carbon dioxide. For example, one mole of ethanol is two moles of carbon and would represent 50 percent $CO_2$-free carbon selectivity to ethanol if four moles of carbon monoxide were converted into one mole of ethanol with the remaining two moles of carbon monoxide measured converted to products other than carbon dioxide or ethanol Selectivity as used herein refers to $CO_2$-free carbon selectivity.

More preferably, the selectivity to the described oxygenated product is about 40 percent or above and most preferably about 50 percent or above. It is especially preferred that the selectivity to the described product is about 60 percent or above, most especially about 70 percent or above. Preferably, the mixed alcohols fraction is formed in at least about 50 percent $CO_2$-free carbon selectivity and especially greater than about 70 percent.

Preferably, $CO_2$-free carbon selectivity to methanol is less than about one-half the $CO_2$-free carbon selectivity of the $C_{1-10}$ mixed alcohol fraction, more preferably about one-third or less and most preferably about one-fifth or less and especially about one-tenth or less. Especially preferred in the immediately foregoing preferences are the cases where the methanol fraction is compared with the $C_{2-5}$ alcohols fraction.

Obtaining these selectivity values is generally a matter of varying the process conditions and the catalyst composition. For example, to increase conversion within the preferred ranges using the reduced catalyst at hand, the temperature, pressure, GHSV and syngas composition may be conveniently varied to produce the desired result. As conversion increases, the product distribution of mixed alcohols produced usually shifts toward higher molecular weight alcohols. Varying the recycle ratio and monitoring the components recycled may alter selectivity also. For example, to obtain more $C_2+$ alcohols in relation to methanol, methanol may be recycled or added to the syngas feed. Varying the reduced catalyst components themselves may provide the desired selectivity. For example, the addition of the Fischer-Tropsch promoters may obtain the higher selectivities to the $C_2+$ alcohols; the use of the preferred cocatalyst metals may obtain these higher selectivities.

The synthesis gas required for conversion into hydrocarbons can be obtained by methods known in the art. Examples are gasification of hydrocarbonaceous materials such as coal, oils, sludges or natural gas; as a partial combustion by-product; by steam reforming of liquid or gaseous organic materials; through the water gas shift reaction; or a combination of these or others. The components may also be generated separately and combined for the reaction.

In a process for converting the synthesis gas into a product of preponderantly $C_{1-10}$ oxygenated hydrocarbons using the composition as catalyst, reaction conditions and synthesis gas compositions can vary widely so long as such product is produced. Generally, the conditions and compositions will fall within the bounds known to the art.

The molar ratio of hydrogen to carbon monoxide in the synthesis gas can vary over a broad range such that the oxygenated hydrocarbons are produced. Preferable lower limits of the ratio are about 0.2, more preferably about 0.25, most preferably about 0.5 and especially about 0.7. Equivalent preferable upper limits are about 100, more preferably about 5, most preferably about 3 and especially about 1.5.

Pressures are such that the $C_{1-10}$ oxygenated hydrocarbons are produced. Pressures are preferably elevated. Elevated pressures include pressures of about 150 psig (1.05 MPa) and above.

In the normal operating ranges, the higher the pressure at a given temperature, the more selective the process will be to the mixed alcohols. A more preferred minimum pressure for $C_{1-10}$ mixed alcohols production is about 500 psig (3.55 MPa). An even more preferred minimum for the mixed alcohols production is about 750 psig (5.27 MPa) with about 1,000 psig (7.00 MPa) being a most preferred minimum. While about 1,500 psig (10.45 MPa) to about 4,000 psig (27.7 MPa) is the most desirable range, higher pressures may be used and are limited primarily by cost of the high pressure vessels, compressors and energy costs needed to carry out the higher pressure reactions. Thus, a preferred maximum is about 20,000 psig (138.2 MPa). About 10,000 psig (69.1 MPa) is a more preferred maximum with about 5,000 psig (34.6 MPa) an even more preferred maximum. About 3,000 psig (20.8 MPa) is a most preferred pressure.

Temperatures are such that the $C_{1-10}$ oxygenated hydrocarbons or mixed alcohols are produced. The selectivity to the desired product is also a function of temperature and is interrelated with the pressure function. However, the minimum temperature used is governed by productivity considerations and the fact that at temperatures below about 200° C., volatile catalytic metal carbonyls may form.

Preferably, then, a preferred minimum temperature is about 200° C. A more preferred minimum is about 220° C. A preferred maximum is about 500° C. A more preferred maximum temperature is about 400° C. A most preferred maximum is about 350° C. An especially preferred range of operation is from about 240° C. to about 300° C.

The GHSV of the synthesis gas feed is such that the $C_{1-10}$ oxygenated hydrocarbons are produced and may vary over a very wide range, as is known in the art, preferably from about 50 hour$^{-1}$ to about 20,000 hour$^{-1}$. More preferably, lower limits of GHSV are about 200 hour$^{-1}$, most preferably about 300 hour$^{-1}$. Also, more preferable upper limits of GHSV are about 10,000 hour$^{-1}$ and most preferably about 5,000 hour$^{-1}$. Within the preferred ranges conversion usually decreases as GHSV increases. Concurrently, however, productivity usually increases. Productivity may be measured by mass of product produced per unit volume of catalyst.

The recycle ratio is the ratio of moles of effluent gas after reaction returned to the feed gas to the moles of gases in the fresh feed gas stream. Recycle ratios may vary from zero to any number which results in the formation of product. It is preferable that some recycle occur, more preferably of a recycle ratio of at least about one and most preferably from about one to about three. It is also preferable that at least a portion of the effluent gas recycled contain unconverted hydrogen and carbon monoxide, more preferably after removal of the desired product, water and carbon dioxide and most preferably after even further removal of other by-products formed as desired. The recycle of one alcohols fraction (e.g., methanol) may favor production of another (e.g., $C_{2}+$ alcohols).

Preferably, the co-products formed with the alcohol fraction in the mixed alcohols process are primarily gaseous products. That is, they are preferably primarily $C_{1-4}$ hydrocarbons. Preferably, $C_{5}+$ hydrocarbons are coproduced therein at less than about 20 percent $CO_2$-free carbon selectivity, more preferably at less than 10 percent and most preferably at less than 5 percent. Lower amounts of normally liquid hydrocarbons make the normally liquid alcohols easier to separate from by-products.

Under preferred conditions, the amount of water formed is substantially less than the amount of desired product formed. Preferably, there is less than about 20 weight percent and more preferably less than about 10 weight percent water based on the quantity of desired oxygenated product, especially wherein the desired product is $C_{1-10}$ more especially $C_{1-5}$ and most especially $C_{2-5}$, mixed alcohols. This water may be removed by known techniques.

For example, in a mixed alcohols process, if the water content is about 2 weight percent or less based on mixed alcohols, the water may advantageously be removed by absorption on molecular sieves. At higher water contents, one may use a water gas shift drying step as disclosed in British Pat. Nos. 2,076,015 and 2,076,423 (hereby incorporated by reference). Use of a sulfur tolerant catalyst such as Haldor Topsoe SSK is preferred in the water gas shift drying step.

The composition, which has such high activity in conversion of synthesis gas herein described, may find special employment in conjunction with catalysts of similar selectivity but less activity in a graded activity reactor. Therein, the reactor is loaded along its throughput with catalyst of successively greater and greater activity, allowing the reactor to be run at a nearly constant exotherm, eliminating localized thermal runways or "hot spots" in the catalyst bed, especially in fixed bed reactors. This gradient may be established in discrete zones with a catalyst of similar activity in each zone or in a continuously functionally increasing gradient. A more limited number of discrete zones may be more effective than a higher number (e.g., four in comparison with ten).

To achieve a catalyst of targeted activity and/or selectivity, the catalyst metal of the composition may be varied as herein described or a composition with known high catalytic activity for the desired reaction is physically blended, as by intimate dry mixing, with other catalysts of lower known activity of the invention or otherwise known in the art. It is usually easy to prepare large batches of the composition with uniform catalytic activities and selectivity.

Fluidized bed applications are preferable over fixed bed applications.

SPECIFIC EMBODIMENTS

The following examples are illustrative of the invention. The catalyst metal is maintained the same for comparative purposes.

In the examples, an apparatus is utilized which includes in sequential order three high pressure gas bottles, a manifold, and reactors equipped on the downstream side with a fine metering valve and a rotameter, a sampling manifold and a gas chromatograph. Two bottles contain mixtures of hydrogen, carbon monoxide and nitrogen. Hydrogen sulfide may also be present, and if it is in the feed stream, the examples note the amounts. The third bottle contains hydrogen Each bottle is independently connected to the manifold The manifold is constructed such that any of the three bottles may be used to feed the reactor. Through the sampling manifold the product of each reactor may be piped to the gas chromatograph for analysis.

The compounds used to make the reduced catalysts in the examples are reagent grade or higher purity unless otherwise noted. Reactors are 3 foot long by ½-inch internal diameter stainless steel tubes. Loaded reactors are then brougt: to operating temperature in the presence of hydrogen. Next, syngas feed from one high pressure gas bottle is allowed to flow through the manifold to the reactor. Pressure, flow and temperature are adjusted to operating values. Product analyses are reported in percent $CO_2$-free carbon selectivity.

In all of the examples the components are mixed as indicated. The syngas feed consists of 5 mole percent elemental nitrogen and 95 mole percent carbon monoxide and elemental hydrogen gases. If the example specifies calcining, the mixture is placed in a furnace and heated to 700° C. in flowing air for 12 hours and cooled to 25° C. Then in all examples, 10 cc of cool product is thoroughly mixed with 10 cc of 12 mesh tabular $Al_2O_3$, placed in the reactor in between beds of inert tabular $Al_3O_3$, and reduced at 500° C. in flowing hydrogen for 17 hours. The reduced catalyst composition is then cooled in flowing hydrogen to reaction temperature and the syngas feed is turned on.

Temperatures on stream are maintained between 220° C. and 320° C. Pressures on stream are maintained between 500 psig (3.55 MPa) and 1500 psig (10.45 MPa). GHSV of the syngas feed is reported as corrected to STP and is maintained between 330 hours$^{-1}$ and 1070 hours$^{-1}$.

Example 1—Reduced $MoO_3$/ $Th(NO_3)_2$ $MoO_3$ (2.0 moles) and $Th(NO_3)_2$ (1.0 mole) are thoroughly blended. The mixture is calcined and reduced. The reduced catalyst composition under the following conditions gives the following:

|  | a | b | c |
|---|---|---|---|
| Hours on stream | 104.5 | 128.1 | 163.8 |
| Temperature, °C. | 271 | 260 | 294 |
| Pressure, psig | 1450 | 1450 | 500 |
| GHSV, hours$^{-1}$ | 377 | 448 | 394 |
| $H_2$/CO molar ratio | 0.71 | 0.71 | 0.71 |
| CO conversion, percent | 8.1 | 6.2 | 7.0 |
| $H_2$ + CO conversion, percent | 7.4 | 4.4 | 5.4 |
| Methane, percent | 33.2 | 24.6 | 12.9 |
| Ethane + LPG's, percent | 15.7 | 11.2 | 28.5 |
| $C_{2-4}$ olefins, percent | 0 | 0 | 0 |
| $C_{1-5}$ alcohols, percent (may include other oxygenates) | 57.6 | 69.7 | 71.1 |

Example 2—Reduced MoO$_3$/ThO$_2$

MoO$_3$ (2.0 moles) and ThO$_2$ (1.0 mole) are ball-milled together for 24 hours and thoroughly blended. The mixture is reduced. The reduced composition under the following conditions gives the following:

|  | a | b | c |
|---|---|---|---|
| Hours on stream | 251.5 | 254.0 | 272.0 |
| Temperature, °C. | 223 | 223 | 233 |
| Pressure, psig | 1450 | 1450 | 1450 |
| GHSV, hours$^{-1}$ | 403 | 468 | 1062 |
| H$_2$/CO molar ratio | 0.73 | 0.73 | 0.73 |
| CO conversion, percent | 21.2 | 21.0 | 7.1 |
| H$_2$ + CO conversion, percent | 20.7 | 22.2 | 9.0 |
| Methane, percent | 15.7 | 19.8 | 29.0 |
| Ethane + LPG's, percent | 24.2 | 32.9 | 54.0 |
| C$_{2-4}$ olefins, percent | 1.6 | 2.5 | 5.1 |
| C$_{1-5}$ alcohols, percent (may include other oxygenates) | 68.2 | 57.9 | 26.2 |

Example 3—Reduced MoO$_3$/ThO$_2$/K$_2$CO$_3$

MoO$_3$ (2.0 moles) and ThO$_2$ (1.0 mole) are ball-milled together for 24 hours and thoroughly blended. To the mixture is added an aqueous solution of K$_2$CO$_3$ sufficient to give a catalyst containing 1.5 percent potassium after drying in air and the reduction. The reduced catalyst composition under the following conditions gives the following:

|  | a | b | c |
|---|---|---|---|
| Hours on stream | 3.3 | 9.5 | 33.9 |
| Temperature, °C. | 275 | 305 | 261 |
| Pressure, psig | 1450 | 1450 | 1450 |
| GHSV, hours$^{-1}$ | 390 | 533 | 433 |
| H$_2$/CO molar ratio | 0.70 | 1.06 | 0.70 |
| CO conversion, percent | 25.1 | 80.0 | 16.3 |
| H$_2$ + CO conversion, percent | 25.4 | 68.2 | 16.3 |
| Methane, percent | 14.5 | 26.3 | 13.0 |
| Ethane + LPG's, percent | 34.9 | 62.6 | 22.9 |
| C$_{2-4}$ olefins, percent | 4.3 | 2.5 | 2.9 |
| C$_{1-5}$ alcohols, percent (may include other oxygenates) | 59.1 | 28.4 | 69.4 |

Example 4

MoO$_3$ (3.0 moles) and 1.0 mole each of the following cocatalyst metal oxides are thoroughly blended. Under conditions representative of the other exemplary specific embodiments, each reduced catalyst composition gives the following:

| Catalyst | Temp, °C. | % H$_2$ + CO conversion | % C$_{1-5}$ alcohols |
|---|---|---|---|
| MoO$_3$/Y$_2$O$_3$ | 250–300 | 10–18 | 29–36 |
| MoO$_3$/La$_2$O$_3$ | 250–300 | 19–47 | 15–20 |
| MoO$_3$/Pr$_2$O$_3$ | 250–300 | 5–10 | 43–53 |
| MoO$_3$/Gd$_2$O$_3$ | 250–300 | 4–6 | 40–50 |

We claim:

1. A process comprising contacting a mixture of carbon monoxide and hydrogen with a catalyst consisting of:

(1) a catalyst metal consisting a molybdenum in free or combined form;

(2) a cocatalyst metal selected from the group consisting of thorium, yttrium, lanthanum, gadolinium and praseodymium or mixtures thereof, in free or combined form;

under conditions, including a pressure of at least 500 psig, sufficient to form C$_{1-5}$ alcohols in at least twenty percent CO$_2$ free carbon selectively.

2. The process of claim 1 wherein the cocatalyst metal is thorium.

3. The process of claim 2 wherein the catalyst and cocatalyst metals are present as free metals, oxides, sulfides carbides or mixtures thereof.

4. The process of claim 3 wherein the catalyst and cocatalyst are reduced prior to contact with the mixture of hydrogen and carbon monoxide.

5. The process of claim 4 wherein the C$_{1-5}$ alcohols are formed in at least forty percent CO$_2$ free carbon selectively.

6. The process of claim 5 wherein the C$_{1-5}$ alcohols are formed in at least sixty percent CO$_2$ free carbon selectively.

7. The process of claim 2 wherein the contacting is carried out at a minimum pressure of about 750 psig.

* * * * *

UNITED STATES PATENT AND TRADEMARK OFFICE
CERTIFICATE OF CORRECTION

PATENT NO. : 4,762,858

DATED : August 9, 1988

INVENTOR(S) : Dennis A. Hucul; Rex R. Stevens, both of Midland, Mich.

It is certified that error appears in the above-identified patent and that said Letters Patent is hereby corrected as shown below:

Front page, left column, under the title "U.S. PATENT DOCUMENTS" the line "4,261,864  2/1981  Hargis" should read --4,261,864  4/1981  Hargis--.

Front page, right column, in the "Abstract" the line "levels of a Fisher-Tropsch promoter." should read --levels of a Fischer-Tropsch promoter.--.

Column 2, line 26, insert a "/" between the words "and or" and it should read --and/or--.

Column 2, line 29, the line should read "are not taught. Hydrogen sulfide is taught to affect the."

Column 2, line 50, insert a period between "2" and "5" in the number "84102932 5."  It is supposed to read --84102932.5--.

Column 2, line 62, insert a period after the word "efficient."

Column 3, line 1, delete the space in the word "Id eally" and the word should read --Ideally--.

Column 3, line 60, insert a period after the word "therein." It is the end of a sentence.

Column 4, line 22, insert a "-" before the word "stibines."

Column 4, line 27, delete the "-" between the words "catalyst" and "metal."

Column 5, line 3, the word "peroent" should be --percent--.

UNITED STATES PATENT AND TRADEMARK OFFICE
CERTIFICATE OF CORRECTION

PATENT NO. : 4,762,858

DATED : August 9, 1988

INVENTOR(S) : Dennis A. Hucul; Rex R. Stevens, both of Midland, Mich.

It is certified that error appears in the above-identified patent and that said Letters Patent is hereby corrected as shown below:

Column 7, line 22, the word "suoh" should be --such--.

Column 7, line 42, insert a "-" between the words "Fischer" and "Tropsch."

Column 7, line 51, insert a "," after "500 hour$^{-1}$."

Column 8, line 41, the word "hydrocarbcns" should be --hydrocarbons--.

Column 8, line 54, insert a "," after the word "ethanol."

Column 9, line 19, insert a period after the word "ethanol" because it is the end of a sentence.

Column 10, line 5, the word "hydroqen" should be --hydrogen."

Column 10, line 20, the word "produotion" should be --production--.

Column 11, line 26, insert a "," after $C_{1-10}$."

Column 12, line 9, insert a period after the word "hydrogen." It is the end of a sentence.

Column 12, line 10, insert a period after the word "manifold." It is the end of a sentence.

Column 12, line 20, the word "brougt" should be --brought--.

Column 12, line 36, the formula "$Al_3O_3$" should be --$Al_2O_3$--.

UNITED STATES PATENT AND TRADEMARK OFFICE
CERTIFICATE OF CORRECTION

PATENT NO. : 4,762,858

DATED : August 9, 1988

INVENTOR(S) : Dennis A. Hucul; Rex R. Stevens, both of Midland, Mich.

It is certified that error appears in the above-identified patent and that said Letters Patent is hereby corrected as shown below:

Column 14, line 4, insert the sentence "Each of the mixtures is calcined and reduced." after the word "blended."

Column 14, line 20, the line should read "a catalyst metal consisting of molybdenum in free."

Column 14, line 28, the word "selectively" should be --selectivity--.

Column 14, line 39, the word "selectively" should be --selectivity--.

Column 14, line 42, the word "selectively" should be --selectivity--.

Signed and Sealed this

Seventh Day of March, 1989

Attest:

DONALD J. QUIGG

Attesting Officer

Commissioner of Patents and Trademarks